(12) United States Patent
Feather et al.

(10) Patent No.: US 9,782,605 B2
(45) Date of Patent: *Oct. 10, 2017

(54) ADAPTIVE THERAPEUTIC LIGHT CONTROL SYSTEM

(75) Inventors: Gary A. Feather, Camas, WA (US); M. Ibrahim Sezan, Camas, WA (US); Christopher A. Segall, Camas, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 69 days.

This patent is subject to a terminal disclaimer.

(21) Appl. No.: 12/910,698

(22) Filed: Oct. 22, 2010

(65) Prior Publication Data

US 2012/0101554 A1    Apr. 26, 2012

(51) Int. Cl.
*A61N 5/06* (2006.01)
*H05B 37/02* (2006.01)

(52) U.S. Cl.
CPC ........ *A61N 5/0618* (2013.01); *H05B 37/0218* (2013.01); *H05B 37/0227* (2013.01); *A61N 2005/0628* (2013.01); *Y02B 20/46* (2013.01)

(58) Field of Classification Search
CPC .......... A61N 5/0618; A61N 2005/0626; A61N 2005/0627; A61N 2005/0628
USPC ..................................................... 607/88, 95
See application file for complete search history.

(56) References Cited

U.S. PATENT DOCUMENTS

| | | | |
|---|---|---|---|
| 4,763,971 A * | 8/1988 | Mori ............................. | 607/95 |
| 4,989,600 A * | 2/1991 | Collier .......................... | 607/95 |
| 5,861,717 A * | 1/1999 | Begemann et al. .......... | 315/158 |
| 6,053,936 A * | 4/2000 | Koyama ............... | A61M 21/00 600/27 |
| 6,164,787 A * | 12/2000 | Seki et al. ....................... | 362/1 |
| 6,350,275 B1 * | 2/2002 | Vreman et al. ................. | 607/88 |
| 6,494,899 B1 * | 12/2002 | Griffin et al. .................. | 607/88 |
| 6,554,439 B1 | 4/2003 | Teicher et al. | |
| 6,955,684 B2 | 10/2005 | Savage, Jr. et al. | |
| 7,679,281 B2 | 3/2010 | Kim et al. | |
| 7,736,382 B2 * | 6/2010 | Webb et al. .................... | 607/89 |
| 2002/0113555 A1 * | 8/2002 | Lys et al. ...................... | 315/149 |
| 2005/0015122 A1 * | 1/2005 | Mott et al. ...................... | 607/88 |
| 2005/0107851 A1 * | 5/2005 | Taboada et al. ................ | 607/88 |
| 2007/0060984 A1 * | 3/2007 | Webb et al. .................... | 607/89 |

(Continued)

FOREIGN PATENT DOCUMENTS

| | | |
|---|---|---|
| JP | 2006027534 A | 2/2006 |
| JP | 2009011582 A | 1/2009 |

OTHER PUBLICATIONS

International Search Report, mailed Dec. 27, 2011, in PCT/JP2011/071544, filed Sep. 14, 2011, Sharp Kabushiki Kaisha, 6 pgs.

*Primary Examiner* — John R Downey
(74) *Attorney, Agent, or Firm* — Chernoff Vilhauer McClung & Stenzel, LLP

(57) ABSTRACT

A system for influencing a state of a user including a light source for emitting light influencing the state of the user and a light controller selectively controlling the emission of the light. The emission may include at least one of, the spectrum of said light; the duration of said light; the distribution of said light; the intensity of said light; and the timing of said light. The analysis engine provides a signal to the light controller indicating a desired emission of the light.

17 Claims, 2 Drawing Sheets

(56) References Cited

U.S. PATENT DOCUMENTS

| | | |
|---|---|---|
| 2008/0119912 A1* | 5/2008 | Hayes .............................. 607/88 |
| 2008/0219013 A1 | 9/2008 | Budinger et al. |
| 2008/0275533 A1 | 11/2008 | Powell |
| 2009/0240311 A1 | 9/2009 | Andersen |
| 2009/0326616 A1 | 12/2009 | Aarts et al. |
| 2010/0060195 A1 | 3/2010 | Tsuboi et al. |
| 2010/0174345 A1 | 7/2010 | Ashdown |
| 2011/0144451 A1* | 6/2011 | Robertson ..................... 600/300 |
| 2011/0202114 A1* | 8/2011 | Kessel et al. ................... 607/88 |
| 2012/0209358 A1* | 8/2012 | Feng .............................. 607/90 |

* cited by examiner

ADAPTIVE THERAPEUTIC LIGHT CONTROL SYSTEM

CROSS-REFERENCE TO RELATED APPLICATIONS

Not applicable.

BACKGROUND OF THE INVENTION

The present invention relates generally to a therapeutic light control system.

The biological circadian rhythm in humans control important processes, such as the daily cycle of waking and sleeping. This biological rhythm tends to align its cycle to the external environment, such as the exposure of light modifying the hormone melatonin levels, which are associated with sleep. The melatonin synthesis is reduced when light impacts the retina of the eye. It may be desirable to modify the circadian rhythm to increase the well being of the person.

Aarts et al., U.S. Patent Application Publication 2009/0326616 disclose a system that influences a photobiological state of a person. The system includes a light source, a sensor that senses a first biophysical parameter of a person that is sent to a control circuit which sends a control signal to the light source so as to generate a predetermined photobiological state. The control signal provided by the control circuit is based upon the first biophysical parameter and another parameter, such as a biophysical parameter sensed at a different time.

The foregoing and other objectives, features, and advantages of the invention will be more readily understood upon consideration of the following detailed description of the invention, taken in conjunction with the accompanying drawings.

BRIEF SUMMARY OF THE INVENTION

In one embodiment a system influences a state of a user includes a light source for emitting light influencing the state of the user and a light controller selectively controlling the emission of the light including at least one of, (1) the spectrum of the light; (2) the duration of the light; (3) the distribution of the light; (4) the intensity of the light; and (5) the timing of the light. An analysis engine provides a signal to the light controller indicating a desired emission of the light based upon data associated with the user that is not sensed from the user's body.

DETAILED DESCRIPTION OF PREFERRED EMBODIMENT

While a light system provides wellness benefits to a user, different users tend to have different responses to the application of light. With different users having different responses to the application of light, it is desirable to include a feedback to the system so that the system may be suitably tuned to the particular user's characteristics. While many users will tend to have similar characteristics, most users will have somewhat different responses to the application of light for therapeutic and wellness benefits. With a suitable application of light, selected for the particular user based upon their individual characteristics, the user may achieve the improved health and wellness benefits.

By way of example, suitable exposure to light may provide responses that are shorter term (such as 0-3 hours of exposure) which are generally psychological in nature. For example, the application of an appropriate amount of soothing lights in a proper manner may calm the user and reduce their heart rate. By way of example, suitable exposure to light may provide responses that are longer term (such as several hours to days) which is primarily circadian in nature as controlled by melatonin levels.

Figure 1:
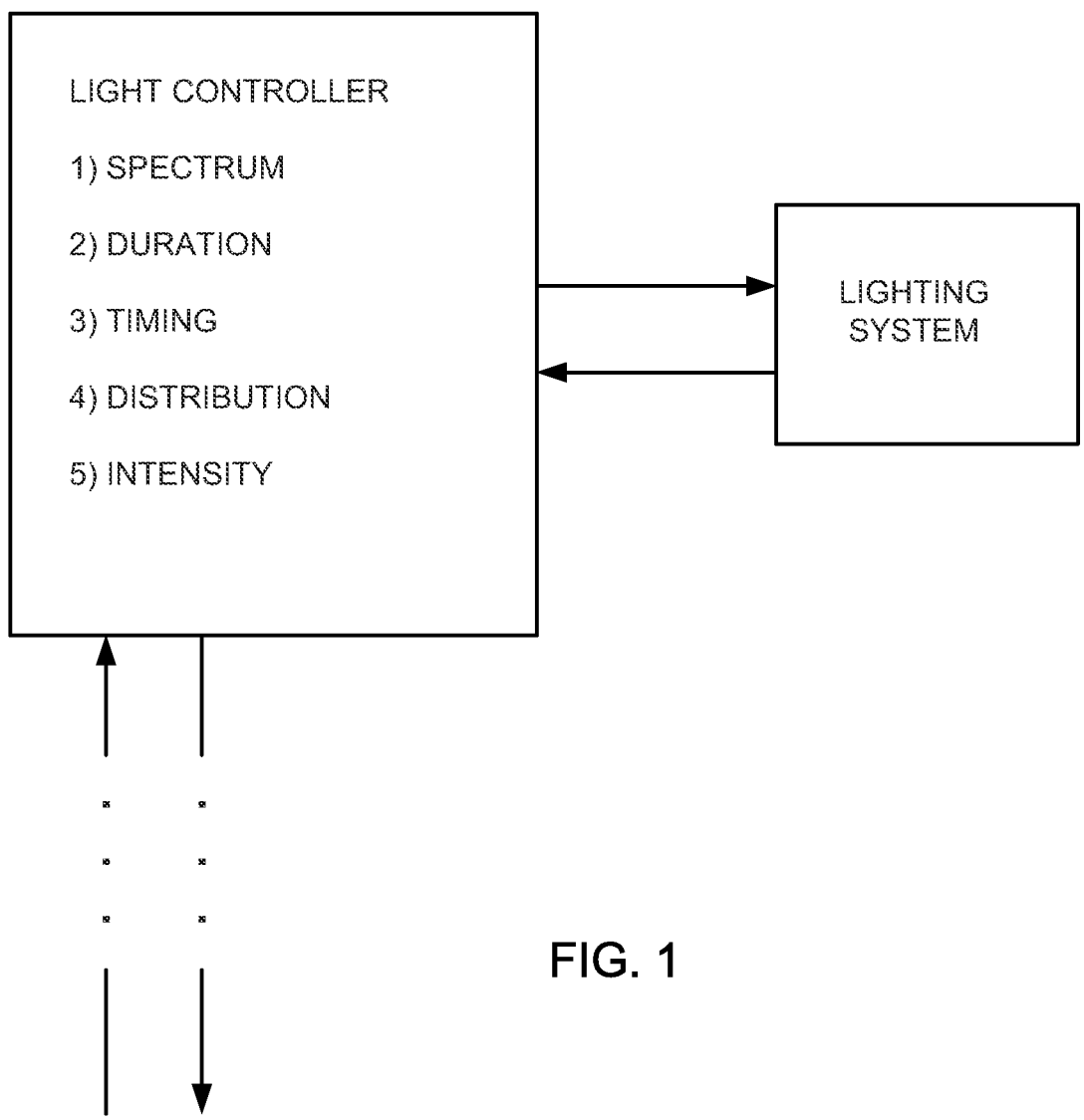
FIG. 1 illustrates a light controller and lighting system.

Referring to FIG. 1, a lighting system may be controlled by a light controller to manage a number of different attributes, each of which may individually or collectively contribute to the wellness and health of a user. The lighting system may include any suitable type of light source, such as for example, a luminaire, ceiling lights, a floor lamp, a desk lap, head worn goggles, a backlit display, or a combination thereof. The lighting system is preferably capable of generating light in the spectrum range of 420 nm to 500 nm for circadian system stimulation, although any spectrum may be used. A first aspect of the lighting system may be the color spectrum of the lights. For example, the lighting system may have multi-colored lights which may be selected to provide desired color or colors to the user. For example, the lighting system may provide a selected color spectrum to the user among a set of different selectable color spectrums including different color temperatures, i.e., warm or cold light. For example, the color spectrum may be modulated or otherwise temporally varied. A second aspect of the lighting system may be the duration of illumination of the lights. For example, the lighting system may provide illumination for one or more selectable durations to the user. A third aspect of the light system may be spatial distributions or positions of one or more of the lights. For example, the lighting system may have a one dimensional light arrangement, a two dimensional light arrangement, or a three dimensional light arrangement where selected lights are illuminated. For example, the lighting system may have a plurality of light sources (or otherwise the distribution of illumination from a light source) that may be spatially and/or temporally selectable. A fourth aspect of the light system may be the brightness of the lights. For example, the lighting system may selectively provide a low illumination to the user, a medium illumination to the user, and/or a high illumination to the user in a manner to contribute to the wellness and the health of the user. For example, the lighting system may selectively have different brightness for different light sources illuminating the user. A fifth aspect of the light system may be the timing of the light or lights. For example, one or more selected lights may be turned on during different parts of the day in different manners.

By selectively modifying one or more of these five different lighting attributes, various wellness and health attributes for the user may be modified. In particular, these modifications should be based upon the particular user so that the most effective wellness and heath benefits may be achieved. By way of example, suitable modification of one or more of these lighting attributes may manage sleep disorders, child hyperactivity learning disorders, elderly safety (e.g., fall avoidance), mental state, and concentration.

Figure 2:
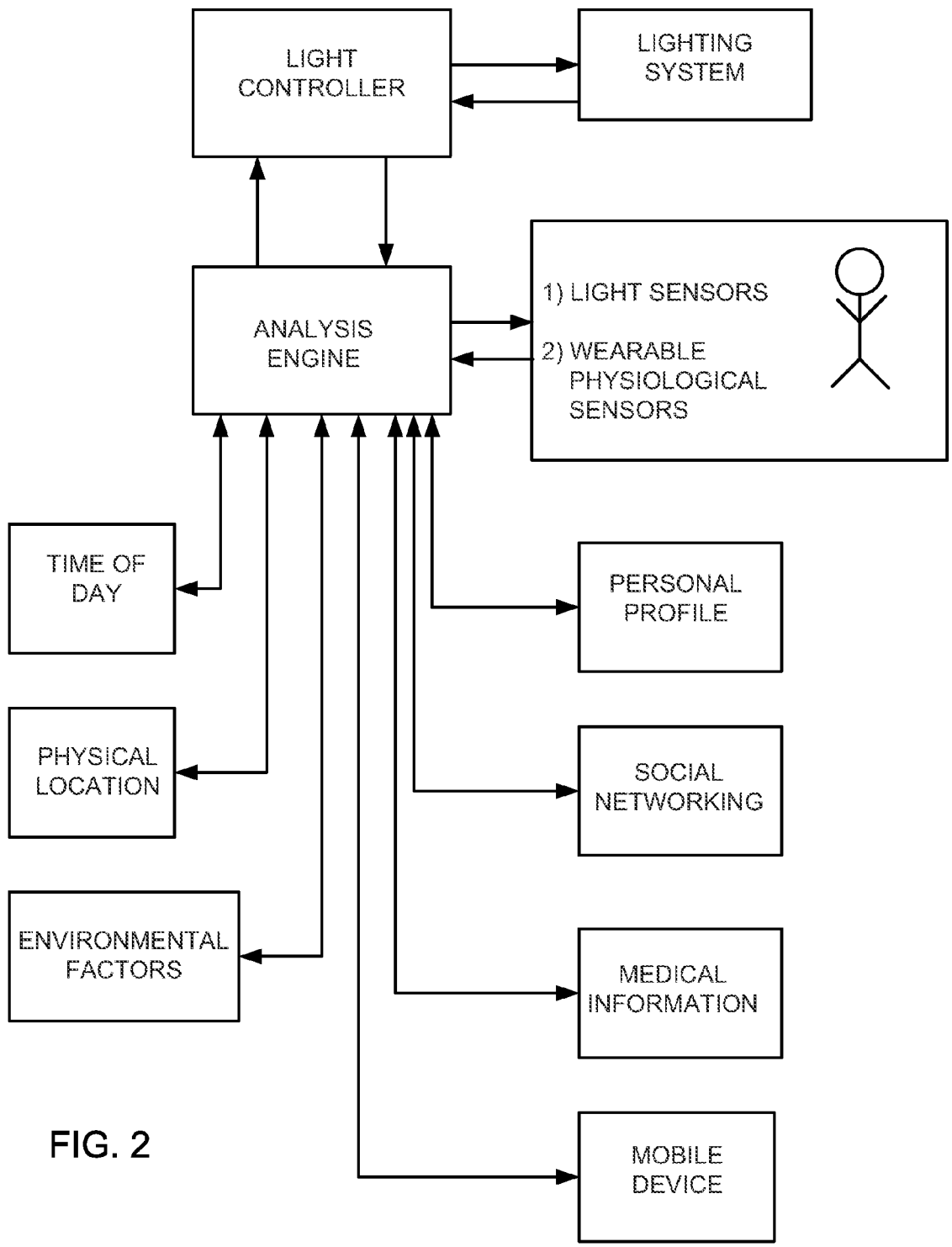
FIG. 2 illustrates a light control system.

Referring to FIG. 2, an analysis engine may be used to selectively control the light controller interconnected to the lighting system. The analysis engine may be operating on a local computer, a service on the Internet, or operating on a cloud computing platform, or otherwise. In some cases, a service provider may be provided to the user to which they may subscribe that provides suitable health services, customizable to the user. The service may be a subscription service to which the user subscribes. The light controller and analysis engine may be separate, or included as separate (or the same) processes on the same device. Also, the different components of the system may be interconnected using any suitable technique, such as wired or wireless communication. The analysis engine may receive input regarding the time of day. The time of day information may be any suitable time based information, such as for example, (1) the current time of the day; (2) morning, afternoon, evening, or night; (3) a weekday or a weekend; (4) a holiday; (5) a particular day of the week; and/or (6) a season of the year. For example, the user may have different requirements in the evening versus the morning. For example the user may have different requirements during the work week rather than the weekend. For example, a holiday may be a stressful time for the user and thus have different requirements than a non-holiday. For example, a user may have different requirements during the winter than the summer.

The analysis engine may also receive input regarding the user's general physical location. For example, a user in Alaska may have different requirements than a user in Colorado, which may likewise be different than the requirements for a user in Hawaii. In addition, the combination of the user's location together with the time of year may have result in different requirements. For example, a user in Alaska during the winter may have different requirements than either a user in Hawaii during the winter or a user in Alaska during the summer. For example, a user being in their home or at the office may result in different requirements.

The analysis engine may also receive environmental factors regarding the user's current environment. Such environmental factors may include, for example, the current weather forecast; whether it is raining; whether it is foggy; whether it is sunny; whether it is overcast; whether it is hailing; whether it is lightening; whether it is flooding; whether it is cloudy; the current temperature; the anticipated temperature; the barometric pressure; and trends with all of the above. The environmental factors may likewise include current social conditions.

The analysis engine may also receive a personal profile of the user. The personal profile may include information particularized to the user. Some of this particular information may include, for example, whether the user is a morning person or an evening person. The information may include an ophthalmologic characterization of the user, which is especially useful when the lighting system administers light using goggles worn close to the user's eyes. The profile may be specific to a particular user, a particular family, a group of people, or otherwise one or more users. The analysis engine may likewise base its processing on more than one profile, such as an average of a pair of profiles. In addition, the profile or profiles to be used by the analysis engine may be selected by a user or automatically selected by the system or otherwise selected based upon other input. Also, the profile may include health information for the user.

In many cases, users do not have the desire or motivation to manually create a profile. In this case, the user may link their profile to a social network account, such as for example, a Facebook account, a Twitter account, or a MySpace account. The analysis engine retrieves personal information from the social networking account, such as, relationship status, birthday, hometown name, hometown location, sex, employer, college, high school, interests, mood, political views, religious views, activities, interests, music, books, movies, television, and/or occupation. In addition, the user may enter information about their current and/or previous status into the social networking service that may be indicative of their state of mind or otherwise. Since a user tends to have friends, acquaintances, or others linked to their social networking account that are similar to themselves, similar information from another's account may be likewise used by the analysis engine. In addition, the personal profile may include a medical profile of the user, or otherwise the personal profile may be linked to an account that includes medical information, preferably medical information that is otherwise periodically updated. Moreover, some of the information in the user profile may be provided by answers to a set of questions. Personal profile may contain information about the mental state of the individual where such state is determined by the answers that the individual provides to a set of questions indicative of individual's focus and alertness. These may include gender, age, activity and/or other profile information The data obtained or otherwise determined as a result of the therapy, together with the results of the therapy, may be provided to the user's medical provider so that they can monitor the therapy. In general, the analysis engine may receive information from a variety of different sources, and may likewise provide information to the sources, as desired.

In some cases, the user's profile may be periodically synchronized from the user's mobile device. By using wireless, Bluetooth, or other communication techniques, the user's mobile device may provide personal information to the analysis engine about the user.

In addition, sensors associated with the user may likewise provide data to the analysis engine. The sensors may include physiological sensors and light sensitive sensors in the environment of the user. Preferably, the light sensitive sensors and the physiological sensors are worn by the user. The physiological sensors may include, for example, heart rate sensors, time sensors, date sensors, location base sensor, acoustic sensor, body temperature sensor, respiration rate sensor, and/or motion sensor. The physiological sensor information accordingly provides information regarding the user's body. For example, if the user's heart rate is elevated then the analysis engine may be used to provide a light signal to reduce the heart rate. Likewise, the analysis engine may use the other information to provide health benefits. The light sensitive sensors, may be for example, a daysimeter device or a camera type sensor.

In some situations, the level or amount of exposure of light to a user in general, or a particular user, may be higher than a suitable level. In many cases, excessive exposure to light may in fact decrease the user's heath. In other cases, a sensor may sense the light exposure level to an individual's retina, and thus check and confirm that safety standards prevent toxicity by controlling light dosage. Accordingly, the analysis engine may use the light sensing information to determine safe lighting levels.

The system may further operate in a close-loop configuration, if desired. The analysis engine while receiving information from many sources, can likewise provide control or feedback signals to lighting controller, and control or feedback signals to the physiological or light sensors and sources of data. For example, the analysis engine could provide feedback for the configuration of the sensors so that they acquire data in a more suitable manner or other configuration data. For example, the analysis engine could provide feedback for goggles worn by the user to control the amount of light received by the user. For example, the analysis engine may update the personal profile with other information. The analysis engine may likewise receive feedback from the light controller and light sensors so that it may monitor the light that is actually provided to the user. For example, the analysis engine may chose to invoke selected sensors to probe specific different characteristics, such as certain sensors placed at certain positions/locations in the house. In this manner, not all of the sensors need to be on at all times or otherwise configured in a particular. Also, the analysis engine also adjusts the sensitivity of individual sensors that are used to collect the data as needed to suitably control the lighting system.

One location that a user spends considerable time is driving a vehicle or a passenger in a vehicle, especially when driving long distances in the vehicle. Within a typical vehicle many different components include light sources, such as overhead lights, instrument panel lights, navigation system lights, and stereo lights. Also, the vehicle may include additional light sources, if desired. The vehicle may likewise include sensors that are provided within the vehicle, such as sensors in the seat, seatbelt, steering wheel, door, floor, pedals, on the driver's body, or otherwise. The analysis engine may use information from these sensors to adjust the lighting that is available in the vehicle though the windows in a manner to improve the health or alertness of the driver. In addition, the analysis engine may modify the sensors or otherwise select sensors. Also, the analysis engine may selectively reduce the external light or increase the external light by modifying the transmission of light into the vehicle. This modification of external light may be achieved, for example, by changing the tint on the windows by an electrical signal, or otherwise raising and lowing a shade over the windows. In many cases, the user enters in a destination into a navigation system that may be used as the basis to provide characteristics of the anticipated drive. Such characteristics may include the travel time, the traffic conditions, the average speed, the acceleration of the vehicle, and other information. The analysis engine may further use this navigation information to modify the lighting to the user in a manner to improve their health or alertness level.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

We claim:

1. A system for influencing a state of a user comprising:
   (a) a light source for emitting light influencing the state of the user;
   (b) a light controller selectively controlling said emission of said light from said light source, including controlling at least one of:
      (1) the spectrum of said light from said light source where said light controller selectively changes said spectrum of said light from a first non-zero range to a second different non-zero range, and;
      (2) the duration of said light emission from said light source where said light controller selectively changes said duration of said light, and;
      (3) the spatial distribution of said light from said light source where said light controller selectively changes said spatial distribution of said light; and
      (4) the timing of said light emission from said light source where said light controller selectively changes said timing of said light; and
      (5) the brightness of said light from said light source where said light controller selectively changes said brightness by modifying the brightness of a plurality of sources of light from said light source;
   (c) an analysis engine providing a signal to said light controller indicating a desired emission of said light; where
   (d) said light controller further automatically modifies without user intervention said emission of said light from said light source based upon said analysis engine, and using feedback received by said light controller and from selective ones of a plurality of light sensors indicative of perceived light provided to the eyes of a user, said feedback based on said system automatically selecting a subset of said plurality of light sensors as being indicative of said perceived light, said subset less than all of said plurality of light sensors.

2. The system of claim 1 further comprising said analysis engine obtaining information from a profile of said user and using said information from said profile of said user to modify said signal to said light controller indicating said desired emission of said light.

3. The system of claim 1 further comprising said analysis engine obtaining information regarding a time of day and using said information regarding said time of day to modify said signal to said light controller indicating said desired emission of said light.

4. The system of claim 1 further comprising said analysis engine obtaining information regarding a physical location of said user and using said information regarding said physical location of said user to select said subset.

5. The system of claim 1 further comprising said analysis engine obtaining information regarding environmental factors of said user and using said information regarding said environmental factors of said user to modify said signal to said light controller indicating said desired emission of said light.

6. The system of claim 1 further comprising said analysis engine obtaining information using a statistical parameter measured from a plurality of different individuals within a social network of said user and using said information to modify said signal to said light controller indicating said desired emission of said light.

7. The system of claim 1 further comprising said analysis engine obtaining information regarding medical information and using said information regarding said medical information to modify said signal to said light controller indicating said desired emission of said light.

8. The system of claim 1 where at least one of said plurality of light sensors is adapted to remain in proximity to a user's retina when selected by said system, while said user moves.

9. The system of claim 1 further comprising said analysis engine obtaining information from a physiological sensor associated with said user and using said information regarding said physiological sensor associated with said user to modify said signal to said light controller indicating said desired emission of said light.

10. The system of claim 1 further comprising:
    (a) a sensor capable of detecting a physiological parameter of said user;
    (b) a light sensor for sensing light; where
    (c) said sensor and said light sensor providing a signal indicative of said physical parameters and said sensed light to said analysis engine.

11. The system of claim 10 further comprising said analysis engine obtaining information from a profile of said user and using said information from said profile of said user to modify said signal to said light controller indicating said desired emission of said light.

12. The system of claim 10 further comprising said analysis engine obtaining information regarding a time of day and using said information regarding said time of day to modify said signal to said light controller indicating said desired emission of said light.

13. The system of claim 10 further comprising said analysis engine obtaining information regarding a physical location of said user and using said information regarding said physical location of said user to modify said signal to said light controller indicating said desired emission of said light.

14. The system of claim 10 further comprising said analysis engine obtaining information regarding environmental factors of said user and using said information regarding said environmental factors of said user to modify said signal to said light controller indicating said desired emission of said light.

15. The system of claim 10 further comprising said analysis engine obtaining information from a social network of said user and using said information to modify said signal to said light controller indicating said desired emission of said light.

16. The system of claim 10 further comprising said analysis engine obtaining information regarding medical information and using said information regarding said medical information to modify said signal to said light controller indicating said desired emission of said light.

17. The system of claim 10 wherein said a light controller selectively controls said distribution of said light based upon said signal from said analysis engine.

* * * * *